US009050056B2

(12) United States Patent
Amit

(10) Patent No.: US 9,050,056 B2
(45) Date of Patent: Jun. 9, 2015

(54) REDUCED X-RAY EXPOSURE BY SIMULATING IMAGES

(71) Applicant: Biosense Webster (Israel), Ltd., Yokneam, IL (US)

(72) Inventor: Matityahu Amit, Zur-Yigal, IL (US)

(73) Assignee: Biosense Webster (Israel) Ltd., Yokneam (IL)

( * ) Notice: Subject to any disclaimer, the term of this patent is extended or adjusted under 35 U.S.C. 154(b) by 111 days.

(21) Appl. No.: 13/726,704

(22) Filed: Dec. 26, 2012

(65) Prior Publication Data

US 2014/0180062 A1 Jun. 26, 2014

(51) Int. Cl.
*A61B 5/00* (2006.01)
*A61B 6/00* (2006.01)
*A61B 6/12* (2006.01)
(Continued)

(52) U.S. Cl.
CPC ... *A61B 6/52* (2013.01); *A61B 6/12* (2013.01); *A61B 6/503* (2013.01); *A61B 6/06* (2013.01); *A61B 6/463* (2013.01); *A61B 6/487* (2013.01); *A61B 6/5247* (2013.01); *A61B 6/5288* (2013.01); *A61B 6/542* (2013.01); *A61B 18/1492* (2013.01); *A61B 2018/00577* (2013.01); *A61B 2019/5238* (2013.01); *A61B 6/4225* (2013.01); *A61B 6/4441* (2013.01); *A61B 6/54* (2013.01); *A61B 5/6876* (2013.01); *A61B 5/0402* (2013.01); *A61B 5/0538* (2013.01); *A61B 5/062* (2013.01); *A61B 5/063* (2013.01); *A61B 2017/00026* (2013.01); *A61B 2017/00088* (2013.01); *A61B 2017/00092* (2013.01); *A61B 2019/5251* (2013.01); *A61B 2018/00357* (2013.01)

(58) Field of Classification Search
CPC ................. A61B 18/1492; A61B 2017/00026; A61B 2017/00088; A61B 2017/0092; A61B 2018/00357
USPC ......... 600/410, 417, 424, 443; 378/4, 62, 115
See application file for complete search history.

(56) References Cited

U.S. PATENT DOCUMENTS 6,226,542 B1 5/2001 Reisfeld
6,301,496 B1 10/2001 Reisfeld
(Continued)

FOREIGN PATENT DOCUMENTS

WO WO 2012/123850 A1 9/2012

OTHER PUBLICATIONS

EP Search Report EP 13 19 9433 Dated March 24, 2014.
(Continued)

*Primary Examiner* — Baisakhi Roy
(74) *Attorney, Agent, or Firm* — Louis J. Capezzuto

(57) ABSTRACT

Medical imaging is carried out by transmitting X-ray emissions through a subject, generating a first set of temporally separated images of an area of interest in the subject from the transmitted X-ray emissions, generating a second set of temporally separated images from the area of interest from a second source, and combining the sets to produce combined images of the area of interest. The method is further carried out by blocking the X-ray emissions from reaching the subject, updating the second set, combining the first set with the updated second set to produce updated combined images, displaying the updated combined images, and when a predetermined condition is satisfied, iterating updating the second set, combining the first set with the updated second set, and displaying the updated combined images.

17 Claims, 3 Drawing Sheets

(51) Int. Cl.
*A61B 6/06* (2006.01)
*A61B 18/14* (2006.01)
*A61B 18/00* (2006.01)
*A61B 19/00* (2006.01)
*A61B 5/0402* (2006.01)
*A61B 5/053* (2006.01)
*A61B 5/06* (2006.01)
*A61B 17/00* (2006.01)

(56) References Cited

U.S. PATENT DOCUMENTS

| | | | |
|---|---|---|---|
| 6,650,927 | B1 | 11/2003 | Keidar |
| 6,814,733 | B2 | 11/2004 | Schwartz |
| 6,892,091 | B1 | 5/2005 | Ben-Haim |
| 6,944,269 | B2 | 9/2005 | Schmitt |
| 6,997,924 | B2 | 2/2006 | Schwartz |
| 7,156,816 | B2 | 1/2007 | Schwartz |
| 7,536,218 | B2 | 5/2009 | Govari |
| 7,756,576 | B2 | 7/2010 | Levin |
| 7,983,383 | B2 | 7/2011 | Kadomura et al. |
| 8,075,486 | B2 | 12/2011 | Tal |
| 2003/0073901 | A1 | 4/2003 | Simon |
| 2007/0086559 | A1 | 4/2007 | Dobbs |
| 2010/0322375 | A1 | 12/2010 | Hirokawa |
| 2011/0021903 | A1 | 1/2011 | Strommer |
| 2011/0164725 | A1* | 7/2011 | Morita et al. ............ 378/62 |
| 2013/0303884 | A1* | 11/2013 | Kuntz et al. ............ 600/417 |

OTHER PUBLICATIONS

U.S. Appl. No. 13/295,594, filed November 14, 2011.

* cited by examiner

REDUCED X-RAY EXPOSURE BY SIMULATING IMAGES

BACKGROUND OF THE INVENTION

1. Field of the Invention

This invention relates to tissue ablation systems. More particularly, this invention relates to tissue ablation systems that involve combinations of fluoroscopic techniques, and non-fluoroscopic imaging techniques.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. The ablation process destroys the unwanted electrical pathways by formation of non-conducting lesions.

SUMMARY OF THE INVENTION

More recently, sophisticated systems of electroanatomic mapping have been used to detect arrhythmogenic areas within the heart and to guide ablation. Fluoroscopy or computed tomography may be used to complement electroanatomic mapping in order to produce a visual reconstruction of the cardiac chambers. An example is described in commonly assigned application Ser. No. 13/295,594, which is herein, which is herein incorporated by reference. A position processor accurately relates the position of the tip of an ablation catheter to target areas using the reconstruction, in order to assure contact between an ablation electrode at the catheter tip and the endocardial surface.

There is provided according to embodiments of the invention a method of medical imaging, which is carried out by transmitting X-ray emissions originating from a first source through a subject, generating a first set of temporally separated images of an area of interest in the subject from the transmitted X-ray emissions, generating a second set of temporally separated images from the area of interest in a second source, and combining the first set and the second set to produce combined images of the area of interest. The method is further carried out by blocking the X-ray emissions from reaching the subject, updating the second set, combining the first set with the updated second set to produce updated combined images of the area of interest, displaying the updated combined images, and when a predetermined condition is satisfied, iterating updating the second set, combining the first set with the updated second set, and displaying the updated combined images.

A further aspect of the method is carried out when the predetermined condition is not satisfied by discontinuing blocking the X-ray emissions from reaching the subject, again generating a first set to produce a new first set, and thereafter iterating blocking the X-ray emissions, updating, combining the first set with the updated second set using the new first set as the first set.

Yet another aspect of the method includes identifying regions in the area of interest having features that have changed subsequent to a previous performance of generating a first set, and discontinuing blocking the X-ray emissions by permitting transmission of the X-ray emissions through the subject to the identified regions while excluding transmission of the X-ray emissions to other portions of the area of interest.

One aspect of the method includes identifying regions in the area of interest having features that are likely to change subsequent to a current performance of generating a first set, and discontinuing blocking the X-ray emissions by permitting transmission of the X-ray emissions through the subject to the identified regions while excluding transmission of the X-ray emissions to other portions of the area of interest.

In an aspect of the method, the steps of blocking and discontinuing blocking the X-ray emissions are performed by disposing a collimator in a path of the X-ray emissions, and adjusting the collimator to regulate the X-ray emissions passing therethrough.

According to an additional aspect of the method, the second set is an electroanatomic map.

One aspect of the method includes introducing a catheter into the area of interest, wherein the second set includes positional information of the catheter.

Still another aspect of the method includes varying the predetermined condition between iterations of generating a first set.

There is further provided according to embodiments of the invention a method of medical imaging, which is carried out by introducing a cardiac catheter into a heart of a subject, activating a fluoroscopic imaging unit having an adjustable collimator and an image intensifier unit to transmit X-ray emissions originating to an area of interest in the heart. The method is further carried out using an image processor by receiving X-ray image data from the image intensifier unit, and generating a first set of temporally separated images of the area of interest from the X-ray image data. The method is further carried out with a cardiac imaging system by generating a second set of temporally separated electroanatomic images from the area of interest, the electroanatomic images including a distal portion of the catheter, combining the first set and the second set to produce combined images of the area of interest, blocking the X-ray emissions from reaching the subject by adjusting the collimator, updating the second set. The method is further carried out with the image processor by combining the first set with the updated second set to produce updated combined images of the area of interest, displaying the updated combined images, and when a predetermined condition is satisfied, iterating updating the second set, combining the first set with the updated second set and displaying the updated combined images.

There is further provided according to embodiments of the invention an apparatus for medical imaging for carrying out the above-described methods.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as USB memory, hard drive, electronic media or CD-ROM. The code may be distributed on such media, or may be distributed to users from the memory or storage of one computer system over a network of some type to storage devices on other computer systems for use by users of such other systems.

Figure 1:
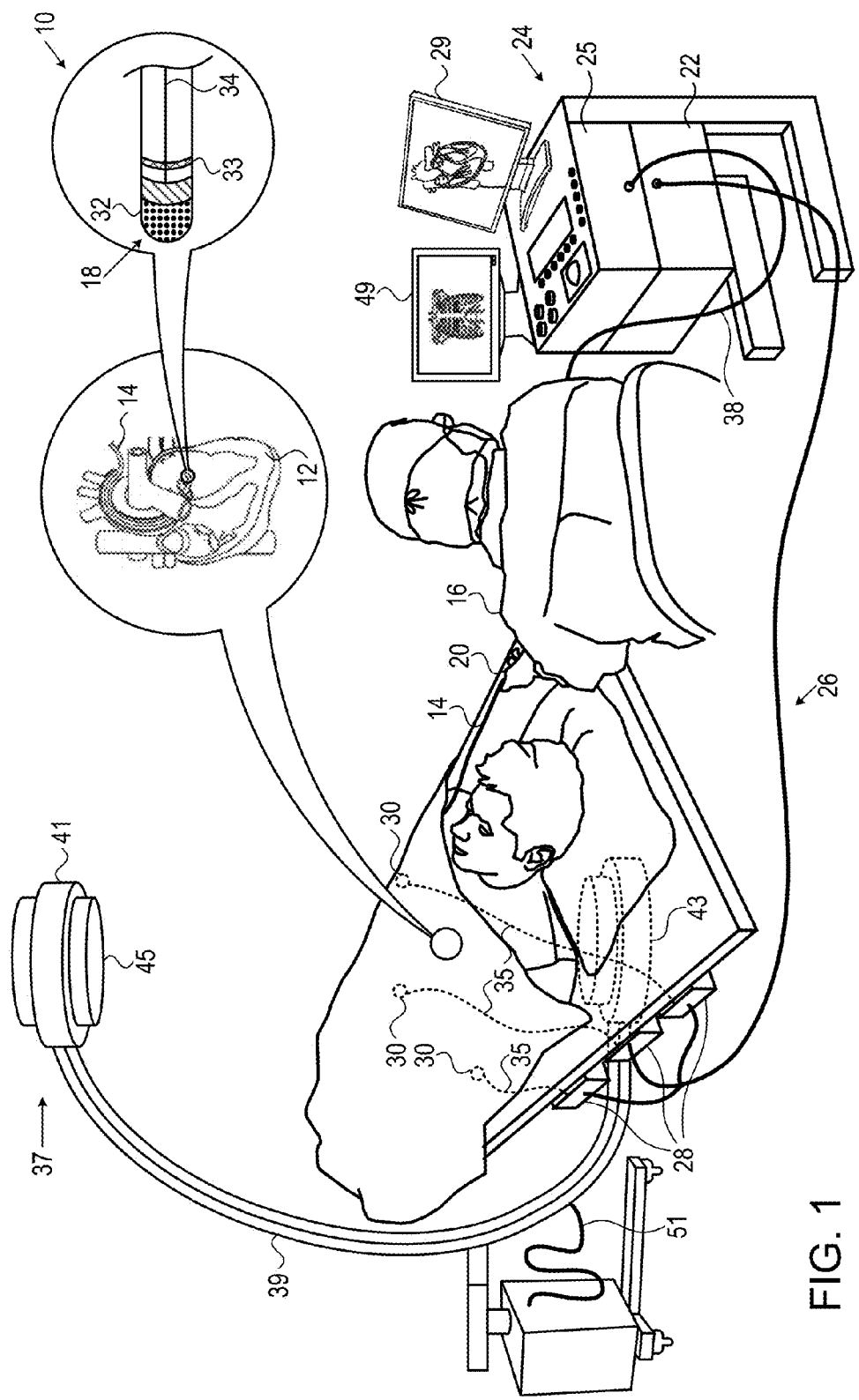
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 23 located in a console 24, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765, which is capable of producing electroanatomic maps of the heart as required for the ablation. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating (or cooling) it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and/or one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, freezing technique and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

A fluoroscopic imaging device 37 has a C-arm 39, an x-ray source 41, an image intensifier module 43 and an adjustable collimator 45. A control processor 47, which may be located in the console 24, allows an operator to control the operation of the fluoroscopic imaging device 37, for example by setting imaging parameters, and controlling the collimator 45 to adjust the size and position of the field of view. The control processor 47 may communicate with the fluoroscopic imaging device 37 via a cable 51 to enable and disable the x-ray source 41 or restrict its emissions to a desired region of interest by controlling the collimator 45, and to acquire image data from the image intensifier module 43. An optional display monitor 49, linked to the control processor 47, allows the operator to view images produced by the fluoroscopic imaging device 37. When the display monitor 49 is not included, the fluoroscopic images may be viewed on a monitor 29, either via a split screen or in alternation with other non-fluoroscopic images.

As noted above, the catheter 14 is coupled to the console 24, which enables the operator 16 to observe and regulate the functions of the catheter 14. The processor 23 is typically a computer with appropriate signal processing circuits. The processor 23 is coupled to drive the monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and analyze the electrical signals from the electrodes, and generate desired electroanatomic maps.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

In order to minimize radiation, the operation of the fluoroscopic imaging device 37 is coordinated with the processor 23. This may be accomplished using a specialized image processor 27, which may be located in the console 24. Alternatively the functions of the image processor 27 may be carried out by the processor 23. In either case composite or sequential alternating images derived from the fluoroscopic imaging device 37 and from the electroanatomic maps are displayed for the operator 16 on the monitor 29. Such images may be gated to the cardiac cycle or non-gated as may be required for the medical procedure.

Operation.

From a safety point of view, exposure to X-ray radiation, both for a patient and for staff in the vicinity of the patient, needs to be minimized. The method described herein helps to minimize the amount of radiation used by applying images produced using the radiation, herein termed "real images," to generate simulated images (also referred to as combined images) that do not directly rely on the radiation. The real images and the simulated images are displayed sequentially on a system monitor, and the interspersal of the two sets of images reduces the overall flux of X-ray radiation, while maintaining a good image quality on the monitor. The interspersal of images may be implemented according to the following flowchart.

Figure 2:
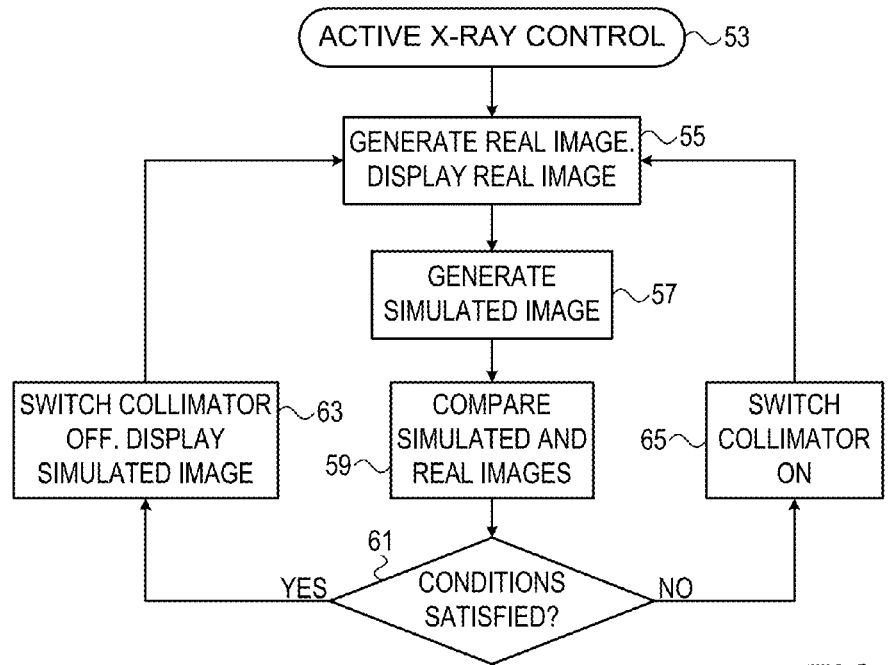
FIG. 2 is a flow chart of a method of image display in accordance with an embodiment of the invention.

Reference is now made to FIG. 2, which is a flow chart of a method of image display in accordance with an embodiment of the invention. The method is described for convenience with reference to the components of the system 10 (FIG. 1), but is not limited to this particular system. The discussion of FIG. 2 sometimes refers for convenience to the CARTO system. However, it will be understood that while this system is suitable for performance of the method, it is not unique, in that other position and image processors, may be acceptable as well.

In initial step 53, it is assumed that the catheter 14 has been introduced into the subject and that the facilities of the fluoroscopic imaging device 37 and the console 24 are operational. An operator activates a control, typically a foot pedal, to activate the fluoroscopic imaging device 37. The subject is exposed to X-ray emissions via the collimator 45. The emissions that pass through the subject are detected in the image intensifier module 43, which transmits signals to the image processor 27.

At step 55 the image processor 27 generates and displays a series of temporally separated X-ray images (referred to herein as "real images" or "real X-ray images"). The framing rate is typically 7.5-15 frames per second. These may be gated according to the cardiac cycle, sequentially displayed, and optionally integrated with other information that is not derived from the X-ray imaging. For example, the integrated images may include locations of catheters derived from the positioning processor 22, which as noted above, can be the above noted CARTO system. Additionally or alternatively, maps and functional information derived from respiration and from the heart beat may be integrated into the real X-ray images, e.g., standard maps generated by the CARTO system, such as a semi-transparent CARTO map, typically gated for heartbeat and respiration, may also be integrated into the real X-ray image. This image is referred to as a "composite image".

At step 57 temporal updates of the CARTO system, (or other mapping system), catheter location are produced, and are received asynchronously with respect to the image sequence produced by the fluoroscopic imaging device 37. The image processor 27 or an optional dedicated simulated image module (not shown) integrates the updates to generate a simulated image. This simulated image is based on temporal updates including: catheter movements (that are learned from the positioning subsystem), movements based on the heart and respiration (that are learned from the mapping system with respiration gating), and movements based on the heart beat (that are based on ECG signal analysis).

Next, at step 59 the image processor 27 compares the most recent composite image generated with the simulated image. These may be displayed on the monitor 29 or on the optional display monitor 49.

Next, at decision step 61, it is determined if the comparison in step 59 satisfies certain preset conditions (described below). If the determination at decision step 61 is affirmative, then control proceeds to step 63. The processor switches the collimator off, i.e., blocks X-ray emissions from reaching the subject and the image intensifier module 43, even though the X-ray control is activated. The simulated image containing the most recent update from the CARTO system is displayed on the monitor 29. Control returns to step 57, where the simulated image module continues to produce simulated images, and, in iterations of step 59, and decision step 61, providing that the preset conditions continue to be satisfied, new simulated images are iteratively displayed in step 63, and the collimator remains off.

If the determination at decision step 61 is negative then control proceeds to step 65. The collimator is switched on, i.e., adjusted to allow X-ray emissions to reach the subject and the image intensifier module 43. Control returns to step 55 and a new series of real X-ray images is generated.

In either case, the process continues so long as the X-ray control remains activated. When the X-ray control is deactivated, the last simulated image generated continues to be displayed on the monitor 29.

Preset Conditions.

Continuing to refer to FIG. 2, the preset conditions mentioned in decision step 61 relate to an acceptable deviation in a simulated image from an ideal registration between the components provided by the fluoroscopic imaging device 37 and the CARTO system. The conditions may be configured or adjusted by the operator, a procedure that may be at least partly guided interactively by the program of the image processor 27.

The inaccuracy or deviation is automatically detected by the image processor 27 in coordination with the CARTO system. Techniques for placing images produced by different modalities in registration are also known from U.S. Pat. Nos. 6,650,927 and 8,075,486, of common assignee herewith, and herein incorporated by reference.

The inaccuracy detected by the system may be a spatial deviation of a feature in the synthetic image, e.g., a determination determining that a particular element of the image, such as the position of a catheter, is incorrect or out of registration by at least a threshold value. For example, the operator may be willing to tolerate up to 2 mm. of spatial deviation as measured in step 59. Alternatively, the inaccuracy may be temporal, e.g., more than 4 s have elapsed since the last real image was taken, and the synthetic image can no longer be guaranteed to be in registration.

Further alternatively, the inaccuracy may be a function of a combination of parameters, e.g., respiratory, circulatory and electrical parameters. For example, the conditions may be satisfied if the spatial inaccuracy is less than 2 mm and the time since the last real image is less than 4 sec, or if the spatial inaccuracy is less than 3 mm and the time is less than 2 sec. Other parameters that may be incorporated into the conditions include the patient breath that is analyzed in the Carto system based on the impedance between back and front patches, heart rate changes, and changes in color or gray level of the image.

Further alternatively, the system can save a bank of generated real images in a database, each in a different phase of the heart beat cycle, and in a variety of heart rate cycles. Each simulated image can be based on the most relevant image from the database.

Alternate Embodiment

The method according to this embodiment limits the subject's total radiation exposure by generation of regional X-ray images within the field of view of the collimator 45. This is done by adjusting the collimator 45 to permit exposure only in particular spatiotemporal regions having features that are likely to have changed state or position or to change in the near future, i.e., within a time interval encompassing new updates from the CARTO system. Making a prediction of regions that are likely to change may be done by compiling and evaluating a historical record of regions that have previously changed during the procedure. Additionally or alternatively, a prediction may be facilitated by employing knowledge of the particular medical procedure being conducted, e.g., by maintaining a knowledge base. For example, it may be deduced from the knowledge base that the distal extremity of the catheter 14 (FIG. 1) is likely to change position. It may also be deduced from recognition of tachypnea in the subject. In addition the system can identify that an update of a specific image is missing in the database, i.e., the latest image in the database is 'old'. Other parameters that may influence the decision include: a determination that the force on the catheter tip/electrodes is sufficient to cause heart wall tenting to occur; and knowledge of the ablation status. During actual ablation the required accuracy is higher. Moreover, performance of algorithms for analysis of perforation risk upon sudden drop in catheter force may further indicate that new real images need to be taken.

For example if a particular feature, e.g., a catheter tip, has changed position in the recent updates from the CARTO system, the next series of X-ray images may be limited to the region of space that is likely to contain the tip. Moreover, if the tip is seen to move only during certain phases of the cardiac cycle, the X-ray exposure may be gated to only include those phases as well as be spatially limited.

Figure 3:
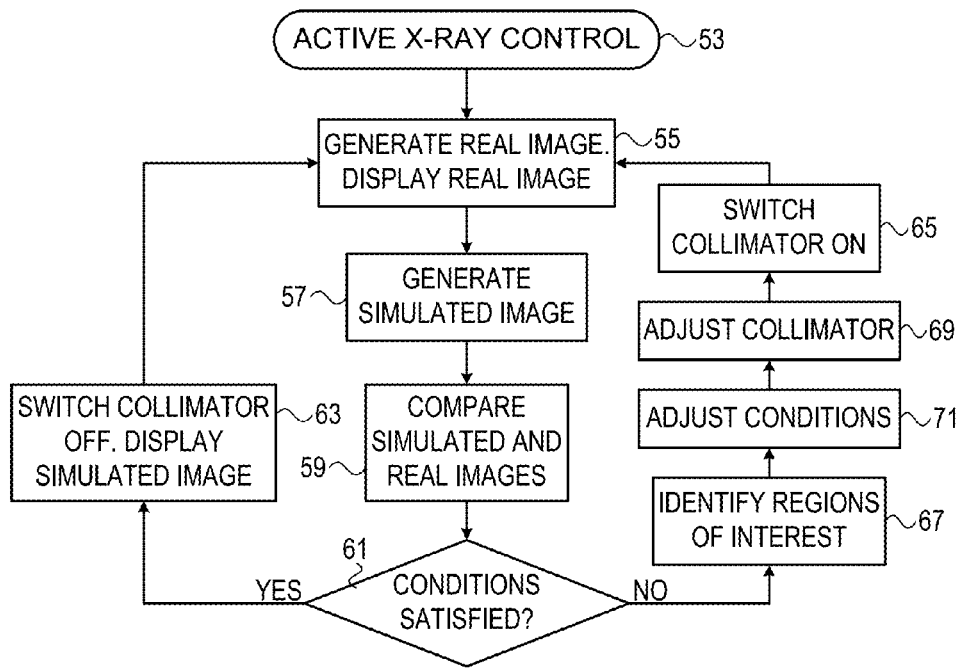
FIG. 3 is a flow chart of a method of image display in accordance with an alternate embodiment of the invention.

Reference is now made to FIG. 3, which is a flow chart of a method of image display in accordance with an alternate embodiment of the invention, and which is explained with continued reference to the example of the system 10 (FIG. 1) for convenience and not by way of limitation. The description of those steps in FIG. 3 that are common to FIG. 2 are not repeated in the interest of brevity.

After performing initial step 53, and steps 55, 57 and 59 as described above, and when the determination at decision step 61 is negative, i.e., the conditions are not satisfied, control passes to step 67. Where regions of the image that have changed state or position are identified by comparison of a historical record of updated images received from the CARTO system. Typically updates spanning the last four seconds are examined. The fluoroscopic images can be transferred based on a DICOM protocol, or based on any other image/video transfer protocol. A prediction is formed of motion-rich regions (formed from previously-transmitted frames). The prediction is subtracted from the current frame to form a residual motion-compensated difference frame, which is then suitably transformed and may be quantized, coded, and processed in the image processor 27 to identify the regions of interest, and optionally transmitted to the monitor 29. Moreover, the coded frame is reconstructed and stored by the image processor 27 for future predictions.

Next, at step 71, the conditions used in decision step 61 may be adjusted, regionally or globally. For example, the spatial conditions may be made more stringent (so that only a small difference between the real and simulated images satisfies the conditions) for a particular region while it is being ablated. The conditions for the region may be relaxed when the region is not being ablated. Of course, if the current conditions are satisfactory, step 71 may be ignored.

Next at step 69, the collimator 45 is adjusted such that the X-ray emissions conform to the regions of interest identified in step 67.

Control then returns to step 55 for another iteration, using regional images as the real images. The process iterates so long as the X-ray control remains activated.

Example

Figure 4:
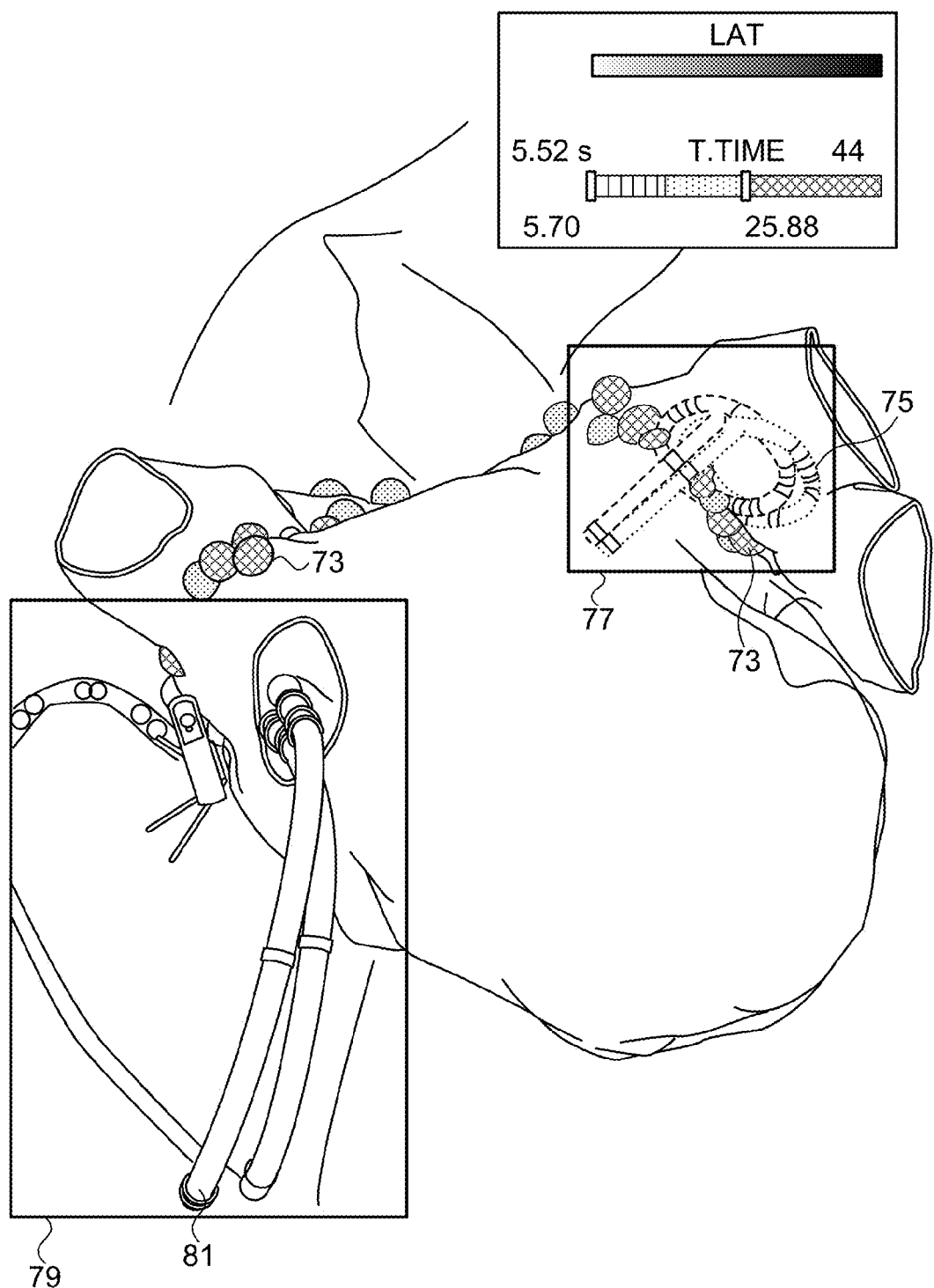
FIG. 4 is a screen display of a simulated image of a heart in accordance with an embodiment of the invention.

Reference is now made to FIG. 4, which is a representative screen display of a composite or simulated image of a heart in accordance with the method described in FIG. 3, wherein the outcome of decision step 61 has required more fluoroscopic images to be obtained. The image of FIG. 4 is shown following completion of step 67. A fluoroscopic image and a Carto image are presented together. A lasso 75 and shaft 81 of a cardiac catheter are shown positioned in the heart as double images, presenting their current position of the lasso 75 and their positions in the previous determination. Two rectangular regions of interest 77, 79 encompass the lasso 75 and the shaft 81, respectively, but do not include other portions of the fluoroscopic image. Subsequent X-ray exposures are to be limited to the regions of interest 77, 79. Since the field of view of a fluoroscopic image can be limited to a particular rectangle, the two regions of interest 77, 79 can be acquired at two different points in time.

It has been found that using the method of FIG. 3, Limiting exposure to regions of interest, e.g., regions of interest 77, 79, can decrease the total radiation exposure by 90%, i.e., the area irradiated by X-rays may be limited to 10% of the total field of view. Furthermore, the avoidance of repeated exposure to X-ray when the determination decision step 61 (FIG. 3) is affirmative can reduce the effective framing rate from a conventional 15 frames per second to about 1.5 frames per sec, because exposure typically occurs only 10% of the time.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of medical imaging, comprising the steps of:
   transmitting X-ray emissions originating from a first source through a subject;
   generating a first set of temporally separated images of an area of interest in the subject from the transmitted X-ray emissions;
   generating a second set of temporally separated images from the area of interest in a second source;
   combining the first set and the second set to produce combined images of the area of interest;
   blocking the X-ray emissions from reaching the subject;
   updating the second set;
   combining the first set with the updated second set to produce updated combined images of the area of interest;
   displaying the updated combined images; and
   when a predetermined condition is satisfied, iterating the steps of updating the second set, combining the first set with the updated second set and displaying the updated combined images, and when the predetermined condition is not satisfied discontinuing blocking the X-ray emissions from reaching the subject, and again performing the step of generating a first set to produce a new first set, and thereafter iterating the steps of blocking the X-ray emissions, updating, combining the first set with the updated second set using the new first set as the first set.

2. The method according to claim 1, further comprising the steps of:
   identifying regions in the area of interest having features that have changed subsequent to a previous performance of the step of generating a first set; and
   performing the step discontinuing blocking the X-ray emissions by permitting transmission of the X-ray emissions through the subject to the identified regions while excluding transmission of the X-ray emissions to other portions of the area of interest.

3. The method according to claim 1, further comprising the steps of:
   identifying regions in the area of interest having features that are likely to change subsequent to a current performance of the step of generating a first set; and
   performing the step discontinuing blocking the X-ray emissions by permitting transmission of the X-ray emissions through the subject to the identified regions while excluding transmission of the X-ray emissions to other portions of the area of interest.

4. The method according to claim 1, wherein the steps of blocking the X-ray emissions and discontinuing blocking the X-ray emissions are performed by disposing a collimator in a path of the X-ray emissions; and
   adjusting the collimator to regulate the X-ray emissions passing therethrough.

5. The method according to claim 1, wherein the second set comprises an electroanatomic map.

6. The method according to claim 1, further comprising the step of:
   introducing a catheter into the area of interest, wherein the second set comprises positional information of the catheter.

7. The method according to claim 1, further comprising the step of varying the predetermined condition between iterations of generating a first set.

8. An apparatus for medical imaging, comprising the steps of:
   An X-ray unit having an image intensifier and an adjustable collimator, the X-ray unit operative for transmitting X-ray emissions via the collimator to an area of interest in a heart of a subject;
   an image processor, receiving X-ray image data from the X-ray unit, and operative for generating a first set of temporally separated images of the area of interest by processing the X-ray image data;
   a cardiac imaging system, operative for generating electroanatomic maps of the heart and positional information of a cardiac catheter introduced therein, the cardiac imaging system operative for generating a second set of temporally separated images from the area of interest, wherein the image processor and the cardiac imaging system are cooperative for performing the steps of:
   combining the first set and the second set to produce combined images of the area of interest;
   blocking the X-ray emissions from reaching the subject;
   updating the second set;
   combining the first set with the updated second set to produce updated combined images of the area of interest;
   displaying the updated combined images; and
   when a predetermined condition is satisfied, iterating the steps of updating the second set, combining the first set with the updated second set and displaying the updated combined images, and when the predetermined condition is not satisfied discontinuing blocking the X-ray emissions from reaching the subject, and again performing the step of generating a first set to produce a new first set, and thereafter iterating the steps of blocking the X-ray emissions, updating, combining the first set with the updated second set using the new first set as the first set.

9. The apparatus according to claim 8, wherein the image processor and the cardiac imaging system are cooperative for performing the further steps of:
   identifying regions in the area of interest having features that have changed subsequent to a previous performance of the step of generating a first set; and
   performing the step discontinuing blocking the X-ray emissions by permitting transmission of the X-ray emissions through the subject to the identified regions while excluding transmission of the X-ray emissions to other portions of the area of interest.

10. The apparatus according to claim 8, wherein the image processor and the cardiac imaging system are cooperative for performing the further steps of:
    identifying regions in the area of interest having features that are likely to change subsequent to a current performance of the step of generating a first set; and
    performing the step discontinuing blocking the X-ray emissions by permitting transmission of the X-ray emissions through the subject to the identified regions while excluding transmission of the X-ray emissions to other portions of the area of interest.

11. A method of medical imaging, comprising the steps of:
    Introducing a cardiac catheter into a heart of a subject;
    activating a fluoroscopic imaging unit having an adjustable collimator and an image intensifier unit to transmit X-ray emissions originating to an area of interest in the heart;

with an image processor receiving X-ray image data from the image intensifier unit, and generating a first set of temporally separated images of the area of interest from the X-ray image data;

with a cardiac imaging system generating a second set of temporally separated electroanatomic images from the area of interest, the electroanatomic images including a distal portion of the catheter;

combining the first set and the second set to produce combined images of the area of interest;

blocking the X-ray emissions from reaching the subject by adjusting the collimator;

updating the second set;

with the image processor combining the first set with the updated second set to produce updated combined images of the area of interest;

displaying the updated combined images; and when a predetermined condition is satisfied, iterating the steps of updating the second set, combining the first set with the updated second set and displaying the updated combined images, and when the predetermined condition is not satisfied discontinuing blocking the X-ray emissions from reaching the subject by readjusting the collimator, and again performing the step of generating a first set to produce a new first set, and thereafter iterating the steps of blocking the X-ray emissions, updating, combining the first set with the updated second set using the new first set as the first set.

12. The method according to claim 11, further comprising the steps of:

identifying regions in the area of interest having features that have changed subsequent to a previous performance of the step of generating a first set; and performing the step discontinuing blocking the X-ray emissions by permitting transmission of the X-ray emissions through the subject to the identified regions while excluding transmission of the X-ray emissions to other portions of the area of interest.

13. The method according to claim 11, further comprising the steps of:

identifying regions in the area of interest having features that are likely to change subsequent to a current performance of the step of generating a first set; and performing the step discontinuing blocking the X-ray emissions by permitting transmission of the X-ray emissions through the subject to the identified regions while excluding transmission of the X-ray emissions to other portions of the area of interest.

14. The method according to claim 11, wherein the predetermined condition comprises a failure of a position of a tip of the catheter in the heart to change during a predetermined time interval.

15. The method according to claim 11, wherein the second set comprises an electroanatomic map.

16. The method according to claim 11, wherein the second set comprises positional information of the catheter.

17. The method according to claim 11, further comprising the step of varying the predetermined condition between iterations of generating a first set.

* * * * *